(12) United States Patent
Xie et al.

(10) Patent No.: US 10,001,442 B2
(45) Date of Patent: Jun. 19, 2018

(54) OPTICAL FIBER-BASED HYBRID SERS PLATFORM FOR IN VIVO DETECTION OF BIO-MOLECULES

(71) Applicant: The Regents of the University of California, Oakland, CA (US)

(72) Inventors: Ya-Hong Xie, Dana Point, CA (US); Pu Wang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 339 days.

(21) Appl. No.: 14/304,290

(22) Filed: Jun. 13, 2014

(65) Prior Publication Data

US 2014/0368817 A1    Dec. 18, 2014

Related U.S. Application Data

(60) Provisional application No. 61/834,556, filed on Jun. 13, 2013.

(51) Int. Cl.
*G01J 3/44* (2006.01)
*G01N 21/65* (2006.01)

(52) U.S. Cl.
CPC ..... *G01N 21/658* (2013.01); *G01N 2021/656* (2013.01)

(58) Field of Classification Search
CPC ... G01J 3/44; G01J 3/02; G01N 21/65; G01N 21/658; G01N 2021/656
USPC ....................................................... 356/301
See application file for complete search history.

(56) References Cited

U.S. PATENT DOCUMENTS

| | | | | |
|---|---|---|---|---|
| 4,778,469 A * | 10/1988 | Lin et al. | ...................... | 128/898 |
| 5,244,711 A * | 9/1993 | Drelich et al. | ................ | 428/113 |
| 5,844,518 A * | 12/1998 | Berg et al. | ......................... | 342/2 |
| 6,168,682 B1 * | 1/2001 | Bennett et al. | ............... | 156/295 |
| 6,194,317 B1 * | 2/2001 | Kaisaki et al. | ................ | 438/692 |
| 6,277,160 B1 * | 8/2001 | Stubbs et al. | ................... | 51/295 |

(Continued)

OTHER PUBLICATIONS

Amezcua-Correa, Adrian et al., "Surface-Enhanced Raman Scattering Using Microstructured Optical Fiber Substrates," Advanced Functional Materials, vol. 17, Issue 3, Sep. 2007, WILEY-VCH Verlag GmbH & Co., pp. 2024-2030.

(Continued)

*Primary Examiner* — Tarifur Chowdhury
*Assistant Examiner* — Md M Rahman
(74) *Attorney, Agent, or Firm* — Withrow & Terranova, P.L.L.C.

(57) ABSTRACT

An optical probe includes an optical fiber with a first end and a second end, and an enhanced surface on a portion of the first end of the optical fiber. The enhanced surface includes a patterned base layer including multiple protruding nano-pyramids, an intermediate layer over the patterned base layer, and a graphene layer over the intermediate layer. Using a layer of graphene to cover the enhanced surface increases the sensitivity of a surface-enhanced Raman spectroscopy (SERS) process performed in conjunction with the enhanced surface, and further increases the chemical stability and bio-compatibility of the enhanced surface. Further, placing the enhanced surface at the end of the optical fiber provides a self-contained probe for use with a SERS process, thereby allowing for in-vivo characterization of a sample.

20 Claims, 6 Drawing Sheets

(56) References Cited

U.S. PATENT DOCUMENTS

| | | | |
|---|---|---|---|
| 7,651,863 B2* | 1/2010 | Hulteen et al. | 436/165 |
| 8,132,611 B2* | 3/2012 | Cohn et al. | 164/46 |
| 8,350,251 B1* | 1/2013 | Lowgren et al. | 257/13 |
| 8,664,642 B1* | 3/2014 | Davis | 257/29 |
| 9,001,324 B2* | 4/2015 | Li et al. | 356/301 |
| 2002/0026752 A1* | 3/2002 | Culler et al. | 51/298 |
| 2002/0182397 A1* | 12/2002 | Whatley | 428/297.4 |
| 2004/0181344 A1* | 9/2004 | Stephanopoulos et al. | 702/20 |
| 2005/0135546 A1* | 6/2005 | Ponstingl et al. | 376/305 |
| 2006/0027900 A1* | 2/2006 | Takeuchi et al. | 257/675 |
| 2006/0038990 A1* | 2/2006 | Habib et al. | 356/301 |
| 2006/0046458 A1* | 3/2006 | Gaska et al. | 438/602 |
| 2006/0057707 A1* | 3/2006 | Cunningham et al. | 435/287.1 |
| 2006/0192115 A1* | 8/2006 | Thomas et al. | 250/306 |
| 2007/0298168 A1* | 12/2007 | Ajayan et al. | 427/249.1 |
| 2008/0006319 A1* | 1/2008 | Bettge et al. | 136/244 |
| 2008/0026583 A1* | 1/2008 | Hardy et al. | 438/693 |
| 2008/0080816 A1* | 4/2008 | D'Urso et al. | 385/77 |
| 2008/0094621 A1* | 4/2008 | Li et al. | 356/301 |
| 2009/0239059 A1* | 9/2009 | Kipp et al. | 428/323 |
| 2009/0295257 A1* | 12/2009 | Wang et al. | 310/367 |
| 2010/0114514 A1* | 5/2010 | Wang et al. | 702/82 |
| 2010/0116405 A1* | 5/2010 | Kipp et al. | 156/39 |
| 2010/0263898 A1* | 10/2010 | Hebert | 174/2 |
| 2010/0300532 A1* | 12/2010 | Cumpston et al. | 136/259 |
| 2010/0326503 A1* | 12/2010 | Wang et al. | 136/255 |
| 2011/0111304 A1* | 5/2011 | Cui et al. | 429/231.8 |
| 2011/0267608 A1* | 11/2011 | Ou et al. | 356/301 |
| 2011/0284061 A1* | 11/2011 | Vanecek et al. | 136/255 |
| 2012/0001196 A1* | 1/2012 | Choi et al. | 257/76 |
| 2012/0012741 A1* | 1/2012 | Vasylyev | 250/237 R |
| 2012/0086021 A1* | 4/2012 | Wang | 257/84 |
| 2012/0281729 A1* | 11/2012 | Ou et al. | 374/187 |
| 2012/0287427 A1* | 11/2012 | Li et al. | 356/301 |
| 2013/0120748 A1* | 5/2013 | Li et al. | 356/301 |
| 2013/0193404 A1* | 8/2013 | Koppens et al. | 257/ |
| 2013/0281784 A1* | 10/2013 | Ray | 600/205 |
| 2014/0015548 A1* | 1/2014 | Naughton et al. | 324/658 |
| 2014/0342128 A1* | 11/2014 | Haynes et al. | 428/172 |
| 2014/0368817 A1* | 12/2014 | Xie et al. | 356/301 |

OTHER PUBLICATIONS

Darhuber, Anton A. et al., "Principles of Microfluidic Actuation by Modulation of Surface Stresses," Annual Review of Fluid Mechanics, vol. 37, 2005, Annual Reviews, pp. 425-455, 32 pages.

Geβner, R. et al., "The application of a SERS fiber probe for the investigation of sensitive biological samples," The Analyst, vol. 129, Issue 12, 2004, The Royal Society of Chemistry, pp. 1193-1199.

Hohenau, Andreas et al., "Spectroscopy and nonlinear microscopy of Au nanoparticle arrays: Experiment and theory," Physical Review B, vol. 73, Apr. 5, 2006, The American Physical Society, 7 pages.

Kostovski, Gorgi et al., "Sub-15nm Optical Fiber Nanoimprint Lithography: A Parallel, Self-aligned and Portable Approach," Advanced Materials, vol. 23, Issue 4, Jan. 25, 2011, WILEY-VCH Verlag GmbH & Co., pp. 531-535.

Kneipp, K. et al., "Single Molecule Detection Using Surface-Enhanced Raman Scattering (SERS)," Physical Review Letters, vol. 78, No. 9, Mar. 3, 1997, The American Physical Society, pp. 1667-1670.

Liu, Ting et al., "Combined taper-and-cylinder optical fiber probes for highly sensitive surface-enhanced Raman scattering," Applied Physics B, vol. 116, Issue 4, Sep. 2014, Springer, pp. 799-803.

Ma, Ke et al., "In Vivo, Transcutaneous Glucose Sensing Using Surface-Enhanced Spatially Offset Raman Spectroscopy: Multiple Rats, Improved Hypoglycemic Accuracy, Low Incident Power, and Continuous Monitoring for Greater than 17 Days," Analytical Chemistry, vol. 83, Issue 23, Dec. 1, 2011, American Chemical Society, pp. 9146-9152.

Motz, Jason T. et al., "Optical fiber probe for biomedical Raman spectroscopy," Applied Optics, vol. 43, No. 3, Jan. 20, 2004, Optical Society of America, pp. 542-554.

Ricciardi, Armando et al., "Versatile Optical Fiber Nanoprobes: From Plasmonic Biosensors to Polarization-Sensitive Devices," ACS Photonics, vol. 1, No. 1, Jan. 15, 2014, American Chemical Society, pp. 69-78.

Smythe, Elizabeth J. et al., "Optical Antenna Arrays on a Fiber Facet for in Situ Surface-Enhanced Raman Scattering Detection," Nano Letters, vol. 9, No. 3, Mar. 11, 2009, American Chemical Society, pp. 1132-1138.

Wang, Pu et al., "Giant Optical Response from Graphene—Plasmonic System," ACS Nano, vol. 6, No. 7, 2012, pp. 6244-6249.

Wang, Pu et al., "Ultra-sensitive Graphene-Plasmonic Hybrid Platform for Label-Free Detection," Advanced Materials, vol. 25, Issue 35, Sep. 20, 2013, WILEY-VCH Verlag GmbH & Co., pp. 4918-4924.

Yap, Fung Ling et al., "Nanoparticle Cluster Arrays for High-Performance SERS through Directed Self-Assembly on Flat Substrates and on Optical Fibers," ACS Nano, vol. 6, No. 3, Mar. 27, 2012, pp. 2056-2070.

Sanders, Mollye et al., "An enhanced LSPR fiber-optic nanoprobe for ultrasensitive detection of protein biomarkers," Biosensors and Bioelectronics, vol. 61, Nov. 2014, Elsevier B.V., pp. 95-101.

Andrade, Gustavo et al., "Multilayer silver nanoparticles-modified optical fiber tip for high performance SERS remote sensing," Biosensors and Bioelectronics, vol. 25, Issue 10, Jun. 2010, Elsevier B.V., pp. 2270-2275.

Liu, Ting et al., "Fiber surface enhanced Raman scattering sensor based on patterned biphasic gold-silver nanoalloys," Chemical Physics Letters, vol. 553, Nov. 2012, Elsevier B.V., pp. 51-54.

Fan, Meikun et al., "Surface-enhanced Raman scattering (SERS) optrodes for multiplexed on-chip sensing of nile blue A and oxazine 720," Lab Chip, vol. 12, Jun. 2012, Royal Society of Chemsitry, pp. 1554-1560.

Yang, Xuan et al., "Nanopillar array on a fiber facet for highly sensitive surface-enhanced Raman scattering," Optics Express, vol. 20, No. 22, Oct. 22, 2012, Optical Society of America, 8 pages.

Foti, Antonino et al., "A Shape-Engineered Surface-Enhanced Raman Scattering Optical Fiber Sensor Working from the Visible to the Near-Infrared," Plasmonics, vol. 8, Issue 1, Mar. 2013, Springer Science+Business Media, LLC, pp. 13-23.

Liu, Chunyu et al., "A surface-enhanced Raman scattering (SERS)-active optical fiber sensor based on a three-dimensional sensing layer," Sensing and Bio-Sensing Research, vol. 1, Aug. 2014, Elsevier B.V., pp. 8-14.

\* cited by examiner

OPTICAL FIBER-BASED HYBRID SERS PLATFORM FOR IN VIVO DETECTION OF BIO-MOLECULES

RELATED APPLICATIONS

This application claims the benefit of provisional patent application Ser. No. 61/834,556, filed Jun. 13, 2013, the disclosure of which is hereby incorporated herein by reference in its entirety.

GOVERNMENT SUPPORT

This invention was made with Government support under HR0011-13-3-0002 awarded by the U.S. Department of Defense, Defense Advanced Research Projects Agency. The U.S. Government has certain rights in the invention.

FIELD OF THE DISCLOSURE

The present disclosure relates to the identification and/or detection of molecules using spectroscopy, such as Raman spectroscopy. Specifically, the present disclosure relates to an optical probe configured to perform in-vivo surface-enhanced Raman spectroscopy (SERS).

BACKGROUND

Raman spectroscopy is a spectroscopic technique widely used to identify molecules and study rotational and vibrational modes in molecular systems. To perform Raman spectroscopy, a monochromatic beam of light with a fixed wavelength is directed at a sample, and a spectrum of scattered light reflected from the sample is collected as a Raman spectrum. The collected Raman spectrum is then used to characterize the sample, for example, by identifying or detecting one or more molecules therein. Although generally an effective way to characterize a sample, traditional Raman spectroscopy techniques suffer from a relatively low sensitivity. In other words, traditional Raman spectroscopy techniques may be unsuitable for identifying or detecting relatively small concentrations of molecules in a given sample.

One way to improve the sensitivity of traditional Raman spectroscopy techniques is through the use of surface-enhanced Raman spectroscopy (SERS). To perform SERS, a sample is placed on a nano-patterned metal surface, and a monochromatic beam of light with a fixed wavelength is directed incident to the nano-patterned metal surface. The intensity of the spectrum of scattered light reflected from the sample on or near the nano-patterned metal surface can be much higher than that obtained using a traditional Raman spectroscopy technique. Accordingly, SERS is a powerful tool that allows for the detection of molecules in highly diluted solutions, and in some cases, may even enable the detection of a single molecule in a solution. Although highly effective for increasing the sensitivity of traditional Raman spectroscopy techniques, SERS is generally unsuitable for in-vivo detection of target molecules in various environments, as it requires a sample to be placed on the nano-patterned metal surface, which in turn must be arranged in proximity to a light emitting device such that a beam of light can be directed incident to the nano-patterned metal surface. In other words, current SERS techniques require multiple components that must be arranged in a specific fashion (generally requiring a relatively large amount of space) to generate a reliable result, thereby precluding the use of SERS within a given environment. Additionally, the nano-patterned metal surface used in current SERS techniques often suffers from oxidation and/or other degradation problems over time, resulting in a decrease in the intensity of scattered light reflected from the surface. Due to oxidation and/or other degradation, the nano-patterned metal surface is generally only used once, then discarded, resulting in an increase in the operating cost of a SERS system. Finally, the nano-patterned metal surface used in current SERS techniques is generally difficult to manufacture on a large scale, often resulting in high cost, low reproducibility, or both.

Accordingly, there is a need for an improved surface for use with SERS techniques that is highly sensitive, resistive to oxidation and other degradation, and capable of manufacture on a large scale at a reasonable cost. Further, there is a need for a SERS system capable of use for in-vivo and in-vitro applications.

SUMMARY

The present disclosure relates to the identification and/or detection of molecules using spectroscopy, such as Raman spectroscopy. In one embodiment, an optical probe includes an optical fiber with a first end and a second end, and an enhanced surface on a portion of the first end of the optical fiber. The enhanced surface includes a patterned base layer including multiple protruding nano-pyramids, an intermediate layer over the patterned base layer, and a graphene layer over the intermediate layer. Using a layer of graphene to cover the enhanced surface increases the sensitivity of a surface-enhanced Raman spectroscopy (SERS) process performed in conjunction with the enhanced surface, and further increases the chemical stability and bio-compatibility of the enhanced surface. Further, placing the enhanced surface at the end of the optical fiber provides a self-contained probe for use with a SERS process, thereby allowing for in-vivo characterization of a sample.

According to one embodiment, light is delivered to the second end of the optical fiber, and reflections of the light from the enhanced surface are used to detect one or more molecules in contact with the enhanced surface.

According to one embodiment, Raman spectroscopy is used to detect the one or more molecules in contact with the enhanced surface.

In one embodiment, a method includes the steps of providing an optical fiber including a first end and a second end, such that the first end includes an enhanced surface. The enhanced surface includes a patterned base layer including multiple protruding nano-pyramids, an intermediate layer over the patterned base layer, and a graphene layer over the intermediate layer. As discussed above, using a layer of graphene to cover the enhanced surface increases the sensitivity of a surface-enhanced Raman spectroscopy (SERS) process performed in conjunction with the enhanced surface, and further increases the chemical stability and bio-compatibility of the enhanced surface. Further, placing the enhanced surface at the end of the optical fiber provides a self-contained probe for use with a SERS process, thereby allowing for in-vivo characterization of a sample.

According to one embodiment, the method further includes the steps of delivering light into the second end of the optical fiber and detecting the light reflected from the enhanced surface to detect one or more molecules in contact with the enhanced surface.

According to one embodiment, Raman spectroscopy is used to detect the one or more molecules in contact with the enhanced surface.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1:
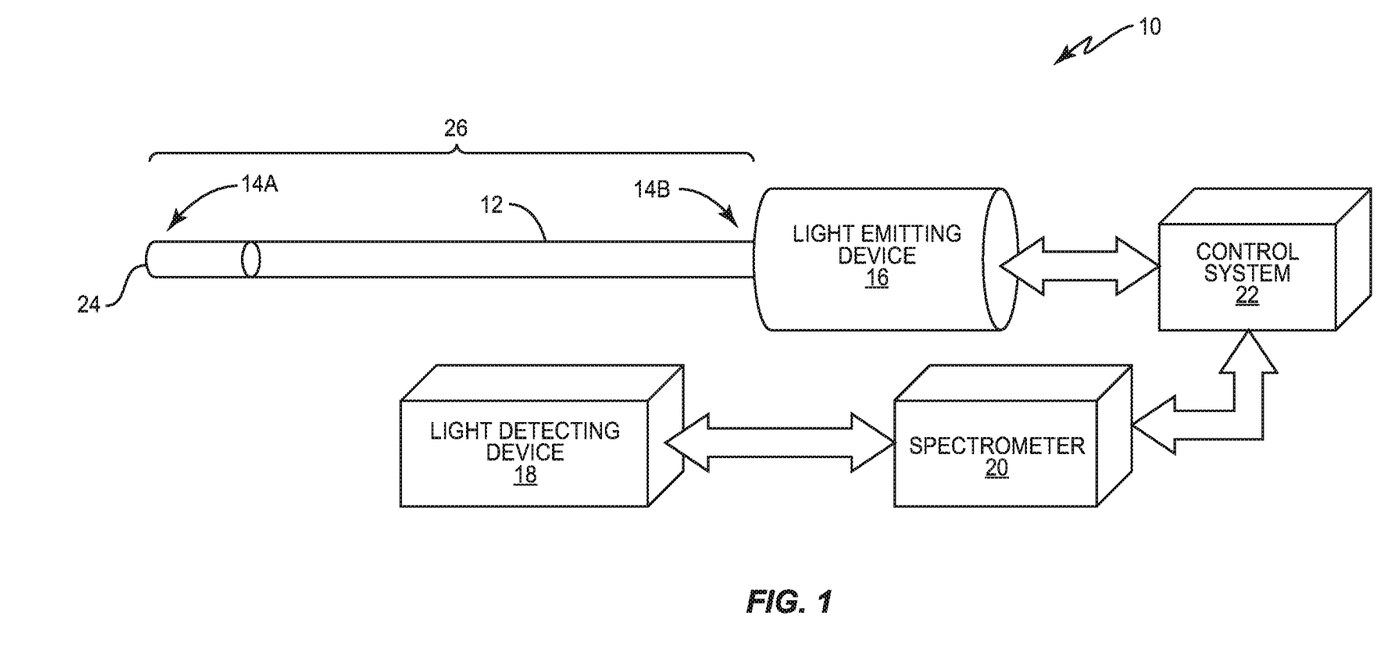
FIG. 1 is a block diagram illustrating a system for performing surface-enhanced Raman spectroscopy (SERS) according to one embodiment of the present disclosure.

Turning now to FIG. 1, a surface-enhanced Raman spectroscopy (SERS) system 10 is shown according to one embodiment of the present disclosure. The SERS system 10 includes an optical fiber 12 including a first end 14A and a second end 14B, a light emitting device 16 coupled to the second end 14B of the optical fiber 12, a light detecting device 18 coupled to the optical fiber 12, a spectrometer 20, and a control system 22. The spectrometer 20 may be in communication with the light detecting device 18 and the control system 22. Further, the control system 22 may be in communication with the light emitting device 16. An enhanced surface 24 may be located on the first end 14A of the optical fiber 12. The optical fiber 12 including the enhanced surface 24 may be referred to as an optical probe 26, an optical sensor, or a SERS sensor herein.

In operation, the control system 22 causes the light emitting device 16 to direct a monochromatic beam of light with a fixed wavelength into the second end 14B of the optical fiber 12. In one embodiment, the light emitting device 16 is a laser; however, those of ordinary skill in the art will appreciate that any suitable light source may be used for the light emitting device 16 without departing from the principles of the present disclosure. The light emitted from the light emitting device 16 is delivered from the second end 14B of the optical fiber 12 to the first end 14A of the optical fiber 12. As light reaches the first end 14A of the optical fiber 12, a portion of the light is reflected from the enhanced surface 24 and/or one or more molecules in contact with the enhanced surface 24 and coupled back into the optical fiber 12. As will be appreciated by those of ordinary skill in the art, the particular spectrum of the light reflected from the enhanced surface 24 and/or the one or more molecules in contact with the enhanced surface 24 (also referred to as a Raman signal or a SERS signal) may indicate one or more characteristics of the molecules in contact with the enhanced surface 24, as discussed in further detail below. The light reflected from the enhanced surface 24 travels back through the optical fiber 12 to the light detecting device 18, where it is delivered to the spectrometer 20. The spectrometer 20 breaks the reflected light into its various components of the electromagnetic spectrum, and relays the resulting information to the control system 22. The control system 22 may then perform a Raman spectroscopy analysis on the resulting information in order to identify, detect, or otherwise characterize one or more of the molecules in contact with the enhanced surface 24 of the optical probe 26.

Because the optical probe 26 is essentially self-contained, the first end 14A of the optical fiber 12 may be physically inserted into a variety of systems or samples for investigation thereof. Accordingly, the SERS system 10 may be especially useful in a biomedical context, such as for in-vivo and/or in-vitro characterization of a living sample or system. In one exemplary embodiment, the optical fiber 12 may be used in-vivo to identify, detect, or otherwise characterize one or more molecules within the human body. For example, the first end 14A of the optical fiber 12 may be placed into the brain tissue of a patient and used to identify, detect, or otherwise characterize one or more neurotransmitters in a specific area of the brain tissue. As will be appreciated by those of ordinary skill in the art, providing a SERS system 10 with a self-contained optical probe 26 opens up a variety of previously unavailable applications for SERS, all of which are contemplated herein.

Although a single optical fiber 12 is shown in the optical probe 26 of FIG. 1, multiple optical fibers may be used in the optical probe 26 without departing from the principles of the present disclosure. For example, a three-ended optical probe fabricated by splicing two optical fibers together may be used, wherein the enhanced surface 24 is on a first end of the three-ended optical probe, the light emitting device 16 is coupled to a second end of the three-ended optical probe, and the light detecting device 18 is coupled to a third end of the three-ended optical probe.

Figure 2A:
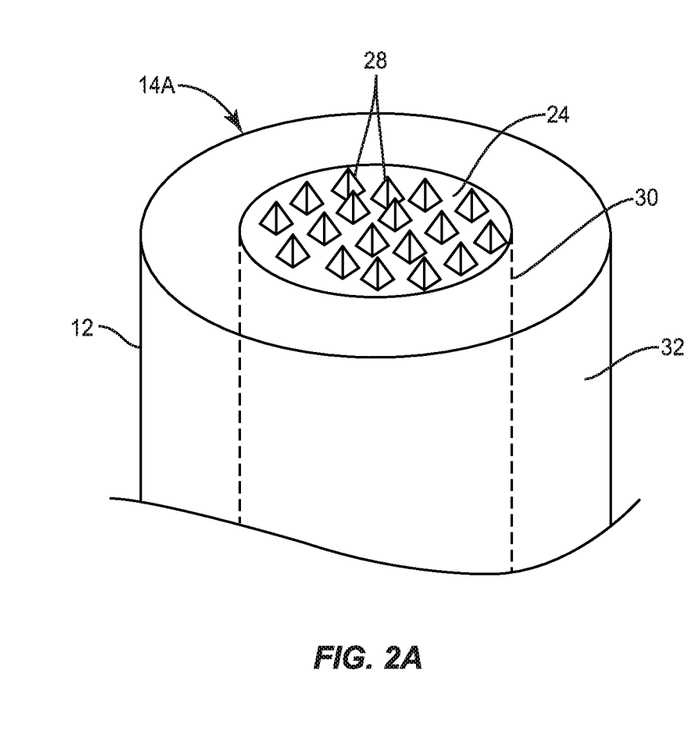
FIGS. 2A and 2B illustrate details of the optical fiber shown in FIG. 1 according to one embodiment of the present disclosure.
Figure 2B:
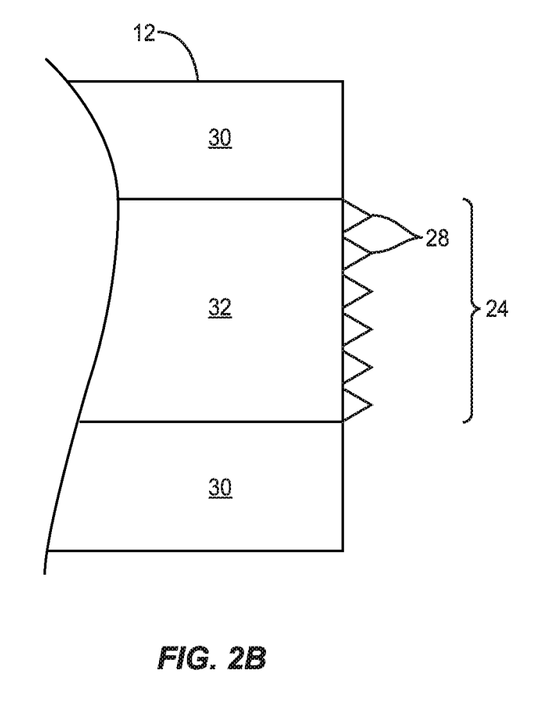

FIGS. 2A and 2B show details of the optical probe 26 according to one embodiment of the present disclosure. As shown in FIG. 2, the first end 14A of the optical fiber 12 includes the enhanced surface 24. The enhanced surface 24 may be a patterned surface including multiple protruding nano-pyramids 28, and may further be covered in a layer of graphene, as discussed in further detail below. As discussed herein, a nano-pyramid refers to a shape including a polygonal base having any number of sides and an apex opposite the base. Although nano-pyramids 28 are shown on the enhanced surface 24 in FIG. 2, any suitable shape may be used to pattern the enhanced surface 24 without departing from the principles of the present disclosure. The optical fiber 12 may include a core 30 and surrounding cladding 32. In one embodiment, the core 30 is used to transport light to the enhanced surface 24 from the light emitting device 16, while the cladding 32 is used to transport light reflected from the enhanced surface 24 and/or one or more molecules in contact with the enhanced surface 24 to the light detecting device 18.

As discussed above, the optical probe 26 is a self-contained device that provides both light and an enhanced surface in order to facilitate a SERS process non-invasively using a relatively small contact area with a given system or sample. Specifically, the first end 14A of the optical fiber 12 is a sealed system that requires only a single point of contact with a sample for the identification, detection, and/or characterization of one or more molecules within the sample. Accordingly, the optical probe 26 may be inserted into a particular environment with ease and without compromising the integrity thereof, making the optical probe 26 especially suited for biomedical applications such as in-vivo or in-vitro measurements.

Figure 3:
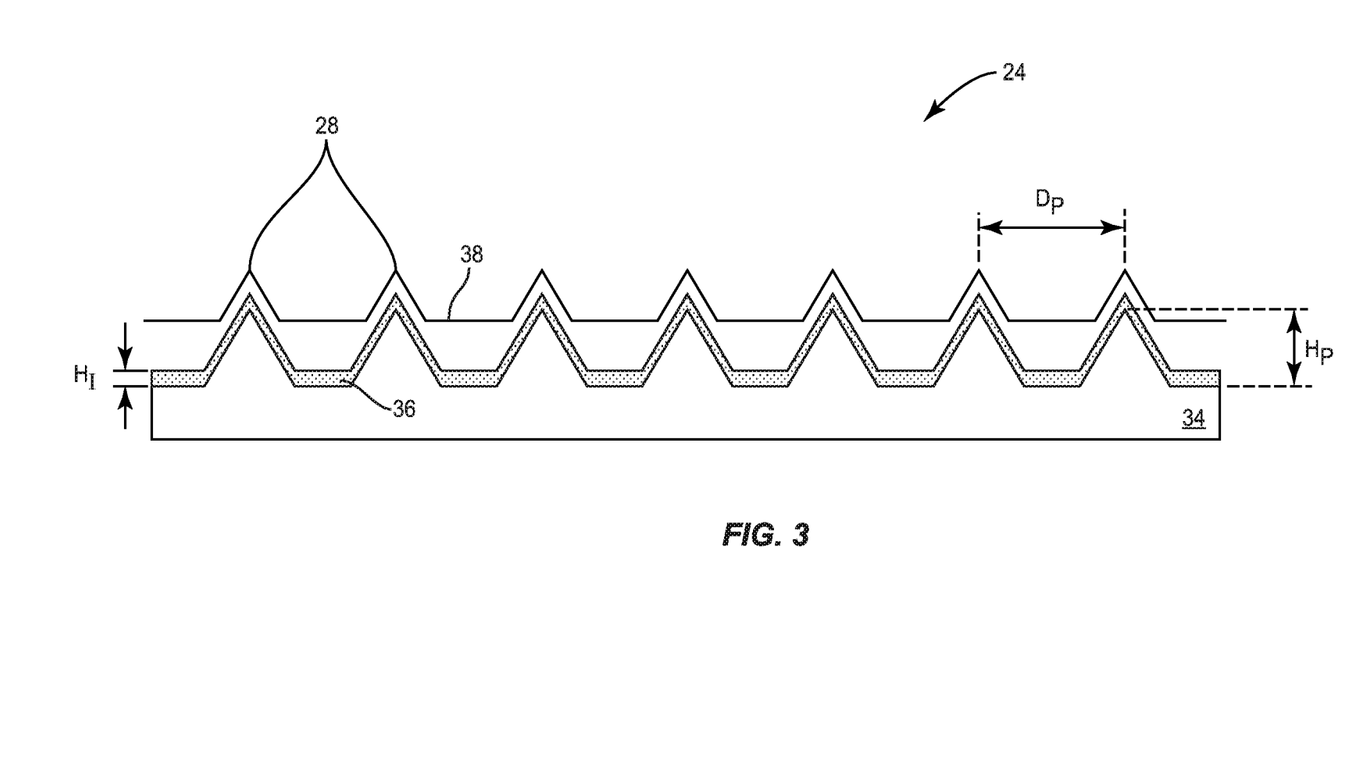
FIG. 3 illustrates details of the enhanced surface shown in FIG. 2 according to one embodiment of the present disclosure.

FIG. 3 shows details of the enhanced surface 24 according to one embodiment of the present disclosure. The enhanced surface 24 includes a patterned base layer 34 including the multiple protruding nano-pyramids 28, an intermediate layer 36 over the patterned base layer 34, and a graphene layer 38 over the intermediate layer 36. In one embodiment, the patterned base layer 34 is a silicon oxide ($SiO_2$), and the intermediate layer 36 is gold (Au). Those of ordinary skill in the art will appreciate that many suitable materials exist for the patterned base layer 34 and the intermediate layer 36, all of which are contemplated herein. In one embodiment, the intermediate layer 36 is about 15 nm thick. The nano-pyramids 28 may be anisotropically shaped and arranged on the enhanced surface 24. That is, each one of the nano-pyramids 28 may be substantially similar in size, such that each one of the nano-pyramids 28 has a height $H_P$ between about 20 nm up to 1 μm. In one embodiment, the height $H_P$ of each one of the nano-pyramids 28 is between about 140 nm to 150 nm. Further, the nano-pyramids 28 may have a substantially uniform topology, such that each one of the nano-pyramids 28 are separated from one another by a distance $D_P$ between about 190 nm and 210 nm, or about 0.707 multiplied by the size of the nano-pyramid.

As will be appreciated by those of ordinary skill in the art, providing the nano-pyramids 28 on the enhanced surface 24 results in an increase in the intensity of the electromagnetic field on the enhanced surface 24 when exposed to light, which in turn increases the intensity of light scattered from the enhanced surface 24 and increases the sensitivity of a SERS process used with the enhanced surface 24. The intermediate layer 36 is provided to boost surface plasmons on the enhanced surface 24 in order to further increase the intensity of light scattered from the enhanced surface 24. Generally, the intermediate layer 36 boosts surface plasmons without influencing the transmittance of light to the enhanced surface 24. As will be appreciated by those of ordinary skill in the art, gold (Au) in particular has been shown to increase plasmonic resonance in various SERS techniques, and therefore may be used for the intermediate layer 36. In other embodiments, different materials may be used for the intermediate layer 36, which may provide different plasmonic resonance characteristics than gold (Au), in order to enhance or accentuate certain characteristics of the molecules on or near the enhanced surface 24.

The height $H_P$ and the distance $D_P$ between the nano-pyramids 28 may be altered in order to produce one or more "hot spots" on the enhanced surface 24, the details of which are discussed above. In other words, the location and density of one or more "hot spots" on the enhanced surface 24 can be controlled via a lithography process, as described in further detail below. As will be appreciated by those of ordinary skill in the art, different heights $H_P$ and distances $D_P$ between each one of the nano-pyramids 28 may exhibit different plasmon resonance characteristics. Specifically, different heights $H_P$ and distances $D_P$ between each one of the nano-pyramids 28 may result in different plasmon resonance frequencies of the enhanced surface 24. As will further be appreciated by those of ordinary skill in the art, different plasmon resonance frequencies of the enhanced surface 24 correspond with an increase in the light scattered from the enhanced surface 24 when different molecules are on or near the enhanced surface 24. Accordingly, the height $H_P$ and the distance $D_P$ between each one of the nano-pyramids 28 may be altered in order to achieve an optimal sensitivity to a given molecule or group of molecules and/or a specific wavelength of light in order to tailor the enhanced surface to a particular application.

To further improve the performance of the enhanced surface 24, the graphene layer 38 is provided over the intermediate layer 36. The graphene layer 38 may further increase the intensity of light scattered from the enhanced surface 24, such that the enhanced surface 24 provides a SERS enhancement factor greater than $10^{10}$ in some cases. Further, the graphene layer 38 may act as a protective coating over the intermediate layer 36, which prevents oxidation of the intermediate layer 36 and therefore preserves the plasmonic enhancement effect thereof. That is, because the graphene layer 38 is chemically inert, it acts as an excellent passivation layer, which can prevent oxidation of the enhanced surface 24 in a variety of ambient and liquid solutions. In addition to preventing oxidation and/or other damage to the intermediate layer 34, the graphene layer 36 is also highly bio-compatible. Accordingly, the optical probe 26 is suited exceptionally well to in-vivo and in-vitro applications, as discussed above. Finally, the graphene layer 38 may be easily refreshed between uses, thereby increasing the longevity of the SERS system 10.

Specifically, the graphene layer 38 increases the intensity of light scattered from the enhanced surface 24 due to both a chemical mechanism (CM) and an electromagnetic mechanism (EM). Regarding the chemical mechanism (CM), the graphene layer 38 results in a charge transfer between the enhanced surface 24 and one or more molecules in contact with the enhanced surface 24. The charge transfer may lead to increased separation between the negative and positive charges of molecules in contact with the enhanced surface 24, which leads to an increase in molecular polarizability that is often associated with larger Raman scattering cross-sections. Additionally, the charge transfer between molecules in contact with the graphene layer 36 may also accentuate certain vibrational characteristics of particular molecules in contact with the enhanced surface 24, which allows further information regarding one or more vibrational modes of the molecules in contact with the enhanced surface 24 to be obtained. Regarding the electromagnetic mechanism (EM), the graphene layer 38 further increases the plasmonic resonance characteristics of the enhanced surface 24, thereby increasing the local (non-propagating) electromagnetic field thereof. Accordingly, the intensity of the light scattered from the enhanced surface 24 may be significantly increased when compared to conventional surfaces used in SERS techniques, which may enable the SERS system 10 to detect very low concentrations of molecules, and even single molecules in a solution.

In addition to the advantages discussed above, the graphene layer 36 further provides an accurate indication of one or more "hot spots" of the enhanced surface 24, even before external molecules are present on the enhanced surface 24. As discussed herein, a "hot spot" is an area on the enhanced surface 24 wherein the intensity of scattered light within the area is exceptionally high. By identifying one or more "hot spots" on the enhanced surface 24, a sample may be directed to a specific "hot spot," thereby increasing the speed and likelihood of identifying, detecting, and/or characterizing molecules within the sample. The presence of the graphene layer 36 itself acts as a "hot spot" indicator, providing an accurate representation of the areas of the enhanced surface 24 in which the intensity of scattered light, and thus the sensitivity of the surface, is the highest. Using the graphene layer 26 to identify one or more "hot spots," which are then used to strategically to identify, detect, and/or characterize a sample allows a SERS process used with the enhanced surface 24 to detect very small concentrations of molecules, and in some cases, even single molecules.

In one embodiment, only a portion of the intermediate layer 36 is covered in graphene. For example, about half of the intermediate layer 36 may be covered with the graphene layer 38, while the other half remains uncovered. As will be appreciated by those of ordinary skill in the art, the different portions of the enhanced surface 24 will react differently with different molecules, and thus may increase the sensitivity of a SERS process used with the enhanced surface 24 for a wider variety of molecules. In one embodiment, two optical probes 26 are included in the SERS system 10, such that one of the optical probes 26 includes the graphene layer 38 and the other does not. Accordingly, the SERS system 10 may identify, detect, and/or characterize a wider variety of molecules.

In an additional embodiment, the graphene layer 38 may be replaced by a number of different van der Waals materials such as hexagonal boron nitride (hBN), molybdenum disulfide ($MoS_2$), and the like. As will be appreciated by those of ordinary skill in the art, van der Waals materials are generally sufficiently thin as to allow for essentially undisrupted electromagnetic energy from plasmonic resonance on the enhanced surface 24 to penetrate through to enable SERS detection. Different van der Waals materials may be used on different portions of the intermediate layer 36, thereby allowing for the identification, detection, and/or characterization of a wider range of molecules, as discussed above. Specifically, since each one of the van der Waals materials has a different affinity to different molecules, each one of the van der Waals materials may provide a selective sensitivity to the identification, detection, and/or characterization of different molecules.

Figure 4:
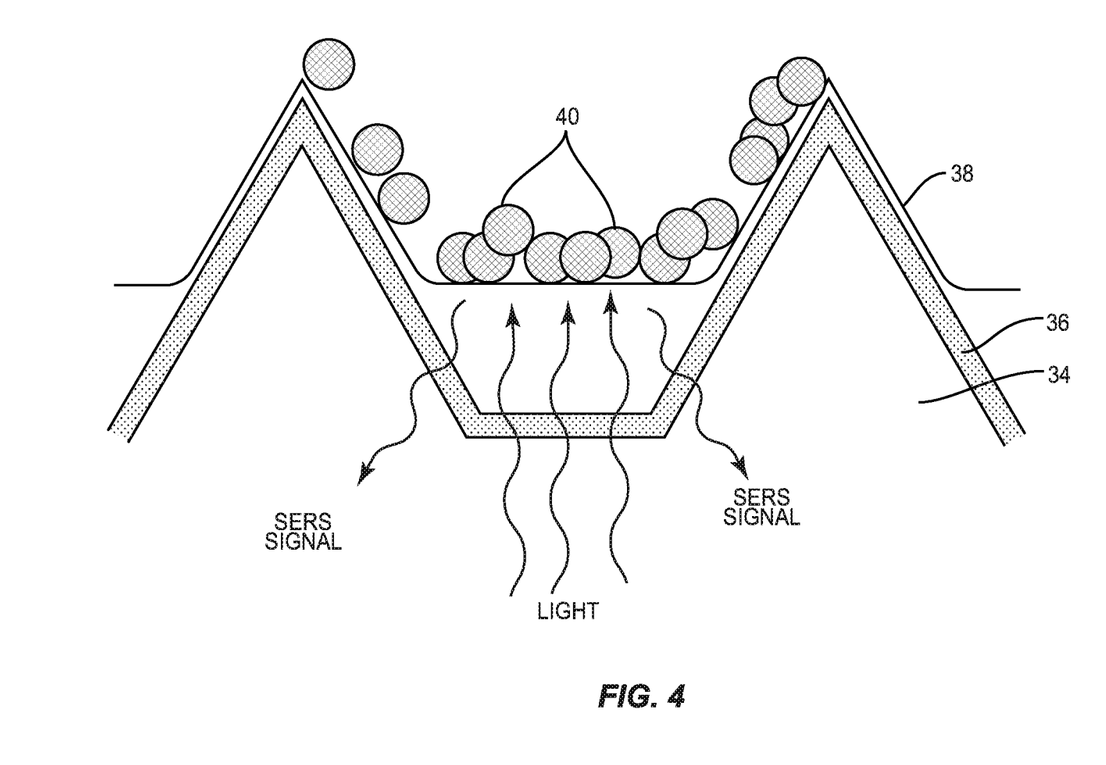
FIG. 4 illustrates further details of the enhanced surface shown in FIG. 2 according to one embodiment of the present disclosure.

FIG. 4 shows details of operation of the SERS system 10 according to one embodiment of the present disclosure. As discussed above, the light emitting device 16 delivers monochromatic light at a desired wavelength into the second end 14B of the optical fiber 12, which is subsequently delivered to the first end 14A of the optical fiber 12. Accordingly, the light (LIGHT) is provided to the backside of the enhanced surface 24. The light passes through the patterned base layer 34, the intermediate layer 36, and the graphene layer 38 to contact one or more molecules 40 in contact with the enhanced surface 24. As will be appreciated by those of ordinary skill in the art, the molecules 40 in contact with the enhanced surface 24 may scatter the light to produce a SERS signal. The scattered light is coupled back into the optical fiber 12, where it is then delivered to the light detecting device 18 and used by the spectrometer 20 to identify, detect, or otherwise characterize the molecules 40 in contact with the enhanced surface 24.

Figure 5:
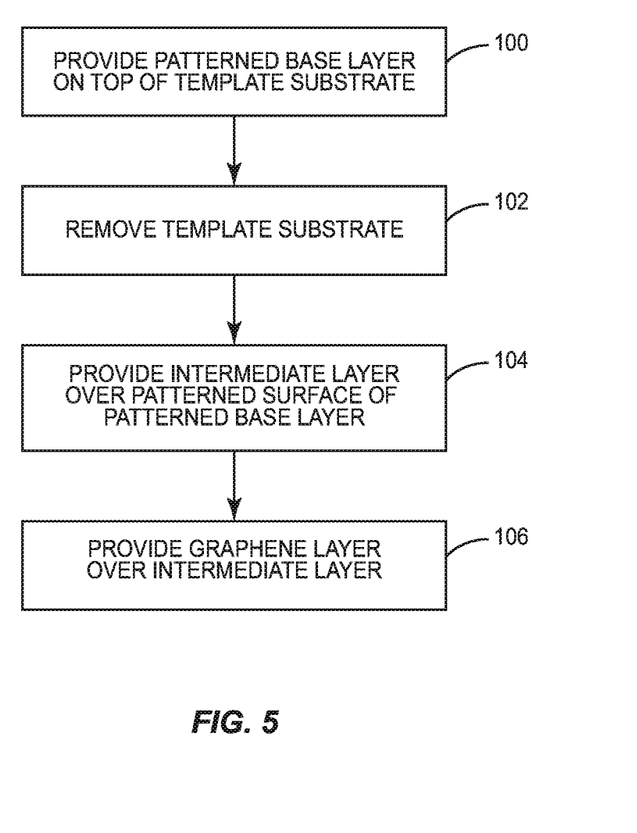
FIG. 5 is a flow diagram illustrating a process for manufacturing the enhanced surface shown in FIG. 2 according to one embodiment of the present disclosure.

FIG. 5 and corresponding FIGS. 6A-6D illustrate a process for manufacturing the enhanced surface 24 according to one embodiment of the present disclosure. First, the patterned base layer 34 is provided on top of a template substrate 42 (step 100 and FIG. 6A). The template substrate 42 may be a silicon substrate including multiple inverted pyramidal pits. In one embodiment, the patterned base layer 34 is provided, for example, by an epitaxial growth process. Those of ordinary skill in the art will appreciate that many different methods for providing the patterned base layer 34 exist, all of which are contemplated herein. Using the template substrate 42 to produce the nano-pyramids 28 for the enhanced surface 24 is a highly reliable process that is reproducible on a large scale with a minor amount of variance. Further, the template substrate 42 may be used with well-known and widely available semiconductor fabrication techniques, thereby reducing the cost in producing the patterned base layer 34 and thus the enhanced surface 24. Next, the template substrate 42 is removed, for example, by an adhesion and peeling process (step 102 and FIG. 6B). Those of ordinary skill in the art will appreciate that many different methods for removing the template substrate 42 exist, all of which are contemplated herein.

Figure 6A:
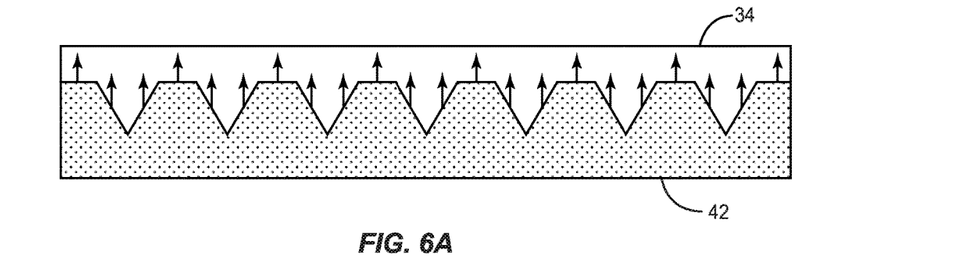
FIGS. 6A-6D illustrate the process shown in the flow diagram of FIG. 5 according to one embodiment of the present disclosure.
Figure 6B:
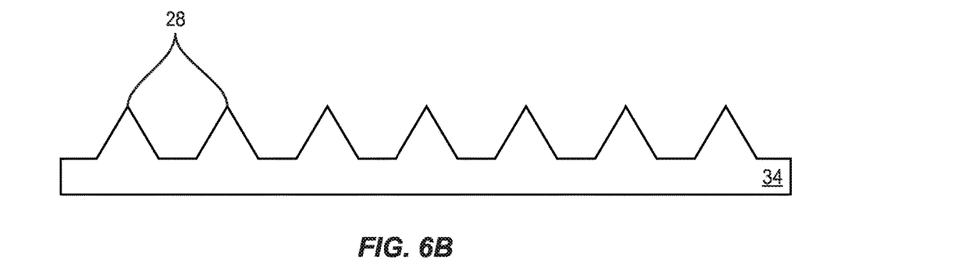
Figure 6C:
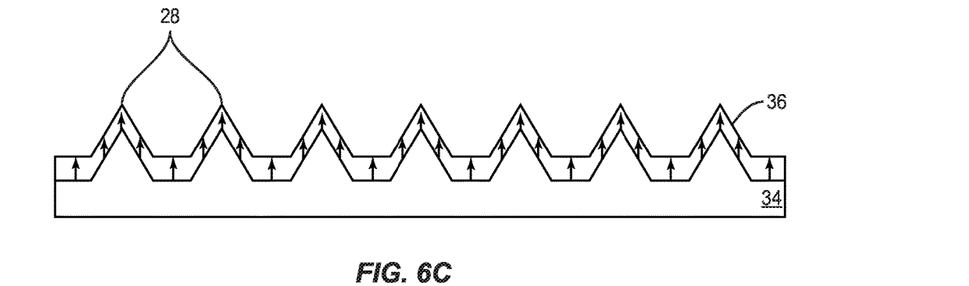
Figure 6D:
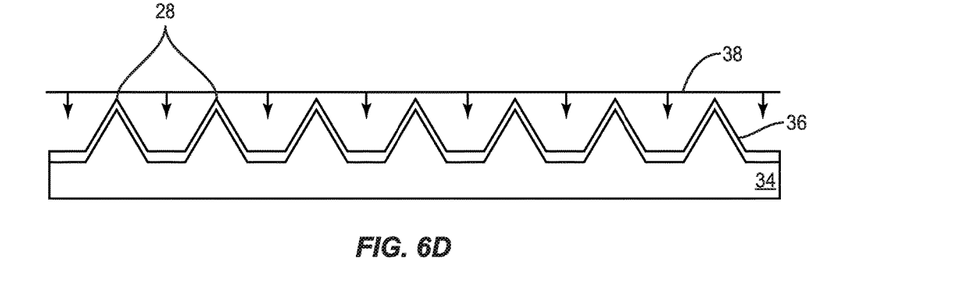

The intermediate layer 36 is then provided over the patterned base layer 34 (step 104 and FIG. 6C). In one embodiment, the intermediate layer 36 is provided by a physical vapor deposition process such as sputtering. Those of ordinary skill in the art will appreciate that many different methods for providing the intermediate layer 36 exist, all of which are contemplated herein. Similar to the above, physical vapor deposition processes such as sputtering are well known and widely available for use, thereby reducing the cost in producing the intermediate layer 36 and thus the enhanced surface 24. Finally, the graphene layer 38 is provided over the intermediate layer 36 (step 106 and FIG. 6D). In one embodiment, the graphene layer 38 is a uniformly grown single graphene layer grown on a copper foil via chemical vapor deposition and transferred to the intermediate layer 36. Once in contact with the intermediate layer 36, the non-uniform surface of the intermediate layer 36 due to the nano-pyramids 28 causes the graphene layer 38 to deform as it conforms to the surface of the intermediate layer 36 via van der Waals forces. Those of ordinary skill in the art will appreciate that many methods for providing the graphene layer 38 over the intermediate layer 36 exist, all of which are contemplated herein.

As discussed above, the graphene layer 38, together with the intermediate layer 36 and the patterned base layer 34, may enhance the signal intensity of light scattered from the enhanced surface 24 more than 1000× greater than that achievable by conventional means due to the enhancement of the localized electromagnetic field between the nano-pyramids 28. Further, the chemically inert graphene layer 38 may protect the intermediate layer 36 and the patterned base layer 34 from oxidation and corrosion, which maintains sensitivity of the enhanced surface 24 over time. Finally, the top-down fabrication approach of the enhanced surface 24 allows for a large degree of reproducibility, resulting in consistent implementation and performance thereof.

Those skilled in the art will recognize improvements and modifications to the preferred embodiments of the present disclosure. All such improvements and modifications are considered within the scope of the concepts disclosed herein and the claims that follow.

What is claimed is:

1. An optical probe comprising:
   an optical fiber including a first end and a second end;
   an enhanced surface on a portion of the first end of the optical fiber, the enhanced surface comprising:
      a patterned base layer including a plurality of protruding nano-pyramids;
      an intermediate layer over the patterned base layer; and
      a graphene layer over the intermediate layer.

2. The optical probe of claim 1 wherein light is delivered to the second end of the optical fiber, and reflections of the light from the enhanced surface are used to detect one or more molecules in contact with the enhanced surface.

3. The optical probe of claim 2 wherein Raman spectroscopy is used to detect the one or more molecules in contact with the enhanced surface.

4. The optical probe of claim 1 wherein the intermediate layer is gold.

5. The optical probe of claim 4 wherein the intermediate layer is about 15 nm thick.

6. The optical probe of claim 4 wherein the patterned base layer is silicon dioxide ($SiO_2$).

7. The optical probe of claim 1 further comprising:
   a light emitting device coupled to the second end of the optical fiber;
   a light detecting device coupled to the second end of the optical fiber; and
   a control system coupled to the light emitting device and the light detecting device.

8. The optical probe of claim 7 wherein:
   the light emitting device is configured to emit light into the second end of the optical fiber;
   the light detecting device is configured to detect light reflected from the enhanced surface; and
   the control system is configured to analyze the light detected by the light detecting device and detect one or more molecules in contact with the enhanced surface based on the detected light.

9. The optical probe of claim 8 wherein Raman spectroscopy is used to detect the one or more molecules in contact with the enhanced surface.

10. The optical probe of claim 9 further comprising a spectrometer between the light detecting device and the control system, the spectrometer configured to measure the spectrum of the light detected by the light detecting device and deliver the spectrum information to the control system.

11. A method comprising:
    providing an optical fiber including a first end and a second end, the first end of the optical fiber including an enhanced surface, wherein the enhanced surface comprises:
       a patterned base layer including a plurality of protruding nano-pyramids;
       an intermediate layer over the patterned base layer; and
       a graphene layer over the intermediate layer.

12. The method of claim 11 further comprising:
    delivering light into the second end of the optical fiber; and
    detecting the light reflected from the enhanced surface to detect one or more molecules in contact with the enhanced surface.

13. The method of claim 12 wherein Raman spectroscopy is used to detect the one or more molecules in contact with the enhanced surface.

14. The method of claim 11 wherein the intermediate layer is gold.

15. The method of claim 14 wherein the intermediate layer is about 15 nm thick.

16. The method of claim 14 wherein the patterned base layer is silicon dioxide ($SiO_2$).

17. The method of claim 11 further comprising:
    providing a light emitting device coupled to the second end of the optical fiber;
    providing a light detecting device coupled to the second end of the optical fiber; and
    providing a control system coupled to the light emitting device and the light detecting device.

18. The method of claim 17 further comprising:
    emitting light from the light emitting device into the second end of the optical fiber;

detecting the light reflected from the enhanced surface using the light detecting device; and analyzing the light detected by the light detecting device and characterizing one or more molecules in contact with the enhanced surface based on the detected light using the control system.

19. The method of claim 18 wherein Raman spectroscopy is used to detect the one or more molecules in contact with the enhanced surface.

20. The method of claim 19 further comprising providing a spectrometer between the light detecting device and the control system, the spectrometer configured to measure the spectrum of the light detected by the light detecting device and deliver the spectrum information to the control system.

* * * * *